(12) United States Patent
Quinn et al.

(10) Patent No.: US 8,167,902 B2
(45) Date of Patent: May 1, 2012

(54) RAPID EXCHANGE CATHETERS FOR EMBOLIC PROTECTION DEVICES

(75) Inventors: Christopher G. Quinn, Minneapolis, MN (US); Sara K. Bakker, Minneapolis, MN (US); Steven G. Zaver, Plymouth, MN (US); Kevin W. Anderson, Brooklyn Center, MN (US); Sengkham Sirivong, Big Lake, MN (US)

(73) Assignee: Tyco Healthcare Group LP, Mansfield, MA (US)

( * ) Notice: Subject to any disclaimer, the term of this patent is extended or adjusted under 35 U.S.C. 154(b) by 1222 days.

(21) Appl. No.: 11/837,056

(22) Filed: Aug. 10, 2007

(65) Prior Publication Data

US 2008/0039817 A1 Feb. 14, 2008

Related U.S. Application Data

(60) Provisional application No. 60/837,378, filed on Aug. 11, 2006.

(51) Int. Cl.
*A61M 29/00* (2006.01)
(52) U.S. Cl. ....................................... 606/200
(58) Field of Classification Search .................... 606/200
See application file for complete search history.

(56) References Cited

U.S. PATENT DOCUMENTS

| 5,257,974 | A | | 11/1993 | Cox |
| 5,843,027 | A | | 12/1998 | Stone et al. |
| 6,096,022 | A | * | 8/2000 | Laymon et al. ............... 604/523 |
| 6,254,610 | B1 | | 7/2001 | Darvish et al. |
| 6,371,970 | B1 | | 4/2002 | Khosravi et al. |
| 6,663,651 | B2 | | 12/2003 | Krolik et al. |
| 6,763,833 | B1 | * | 7/2004 | Khera et al. ................... 128/830 |
| 6,866,677 | B2 | | 3/2005 | Douk et al. |
| 6,902,572 | B2 | | 6/2005 | Beulke et al. |
| 7,104,399 | B2 | * | 9/2006 | Duffy et al. ..................... 206/364 |
| 7,317,951 | B2 | * | 1/2008 | Schneider et al. ............ 607/126 |
| 7,637,920 | B2 | * | 12/2009 | von Lehe et al. .............. 606/200 |
| 7,695,491 | B2 | * | 4/2010 | Clubb ............................ 606/200 |
| 2002/0121472 | A1 | | 9/2002 | Garner et al. |
| 2003/0078519 | A1 | | 4/2003 | Salahieh et al. |
| 2003/0109886 | A1 | | 6/2003 | Keegan et al. |

(Continued)

OTHER PUBLICATIONS

Jan. 30, 2008 Notification of Transmittal of the International Search Report and the Written Opinion of the International Searching Authority, or the Declaration for counterpart International Application No. PCT/US2007/017820 (13 pages).

*Primary Examiner* — Gary Jackson
*Assistant Examiner* — Amy Shipley

(57) ABSTRACT

Catheter having a first elongate tubular body having a lumen, a second elongate tubular body having a lumen, and an elongate member. The elongate member joins the first and second elongate tubular bodies. The first tubular body is fixedly attached on the distal portion of the elongate member, and the second elongate tubular body is disposed on the elongate member is slidable along a portion of the elongate member. The second elongate tubular body can be in a first position so that the first and second tubular bodies are not adjacent to each other and can be in a second position so that the first and second tubular bodies are adjacent to each other. The catheter may have a locking mechanism that can lock the first and second elongate tubular bodies to each other so that the lumens of the first and second elongate tubular bodies form one continuous lumen.

82 Claims, 12 Drawing Sheets

U.S. PATENT DOCUMENTS

| | | |
|---|---|---|
| 2003/0125751 A1 | 7/2003 | Griffin et al. |
| 2003/0212429 A1 | 11/2003 | Keegan et al. |
| 2004/0049226 A1 | 3/2004 | Keegan et al. |
| 2004/0082968 A1 | 4/2004 | Krolik et al. |
| 2004/0167566 A1 | 8/2004 | Beulke et al. |
| 2005/0085842 A1 | 4/2005 | Eversull et al. |
| 2005/0113804 A1 | 5/2005 | von Lehe et al. |
| 2005/0119686 A1 | 6/2005 | Clubb |
| 2005/0131450 A1 | 6/2005 | Nicholson et al. |
| 2006/0030876 A1 | 2/2006 | Peacock, III et al. |
| 2006/0074274 A1* | 4/2006 | Friedman et al. ............ 600/114 |
| 2006/0190025 A1* | 8/2006 | Lehe et al. .................... 606/200 |

* cited by examiner

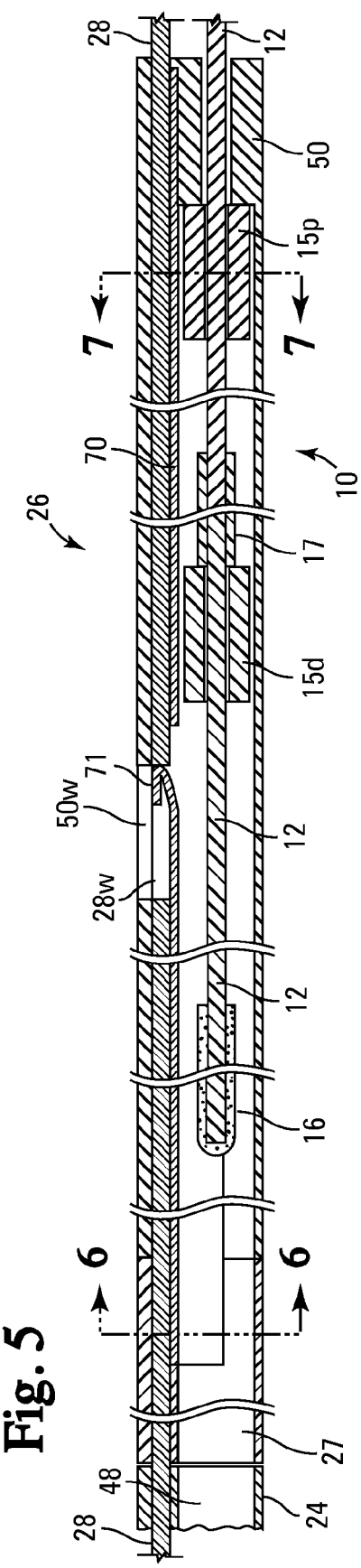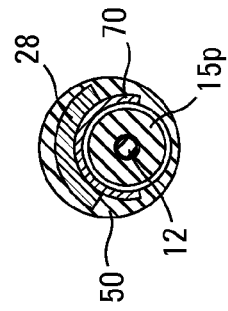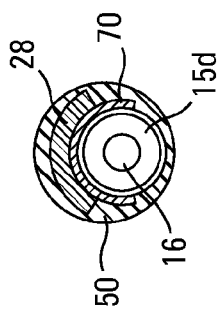

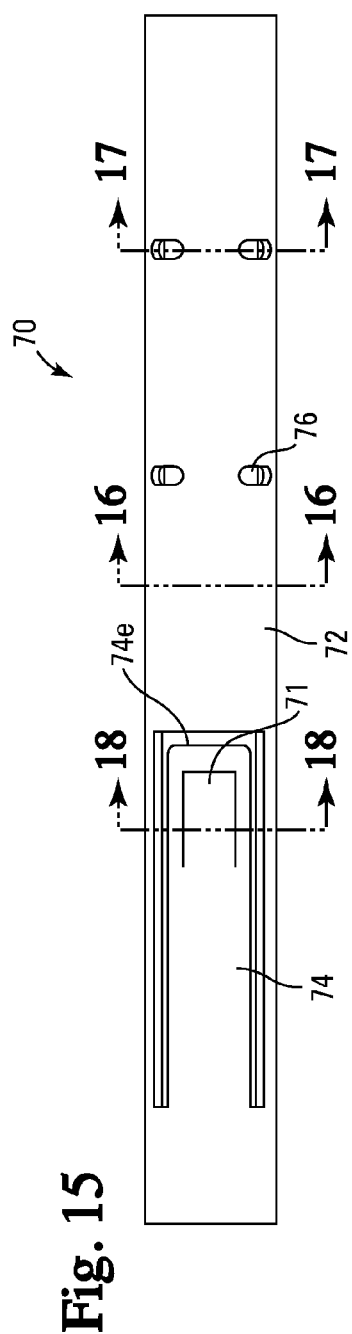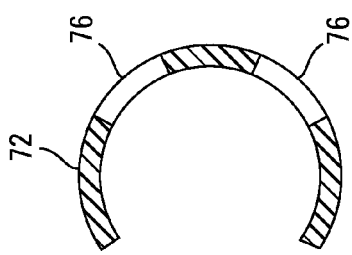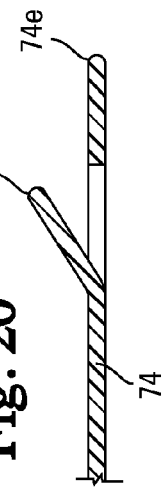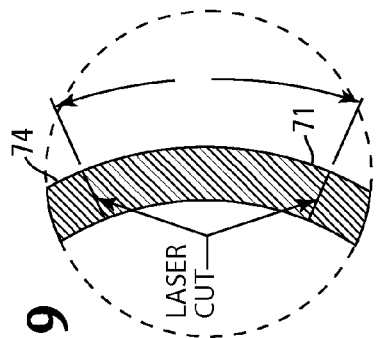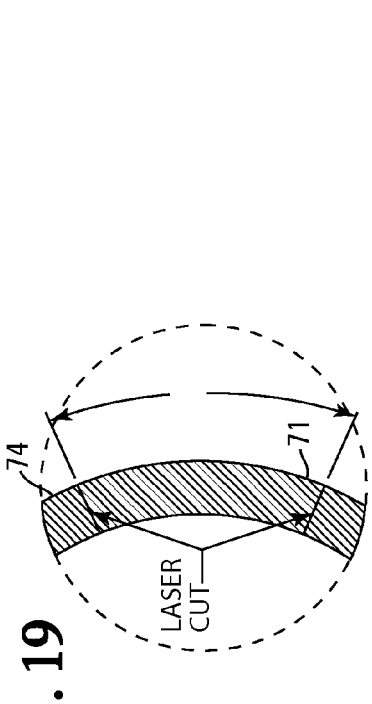

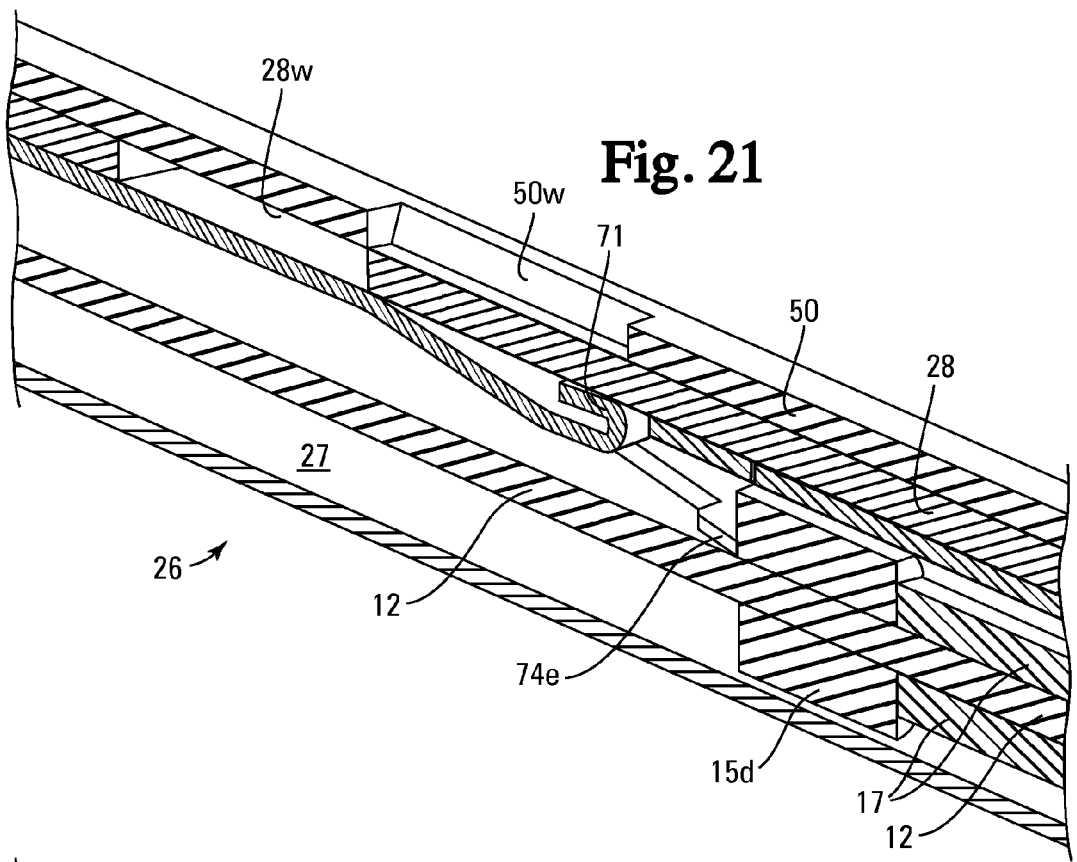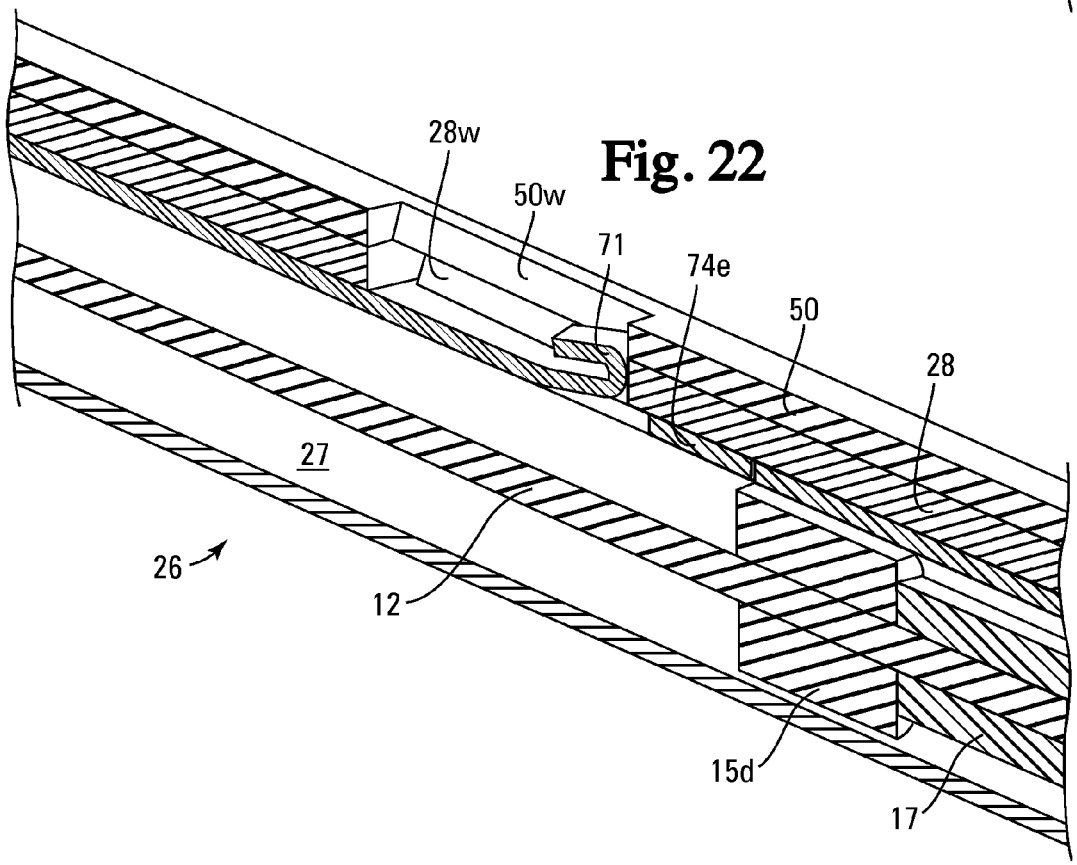

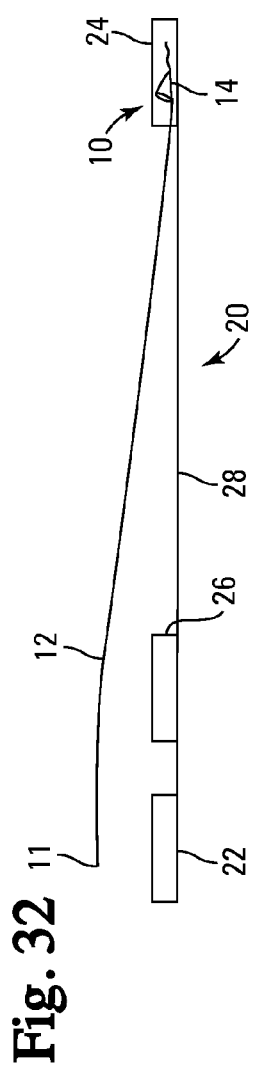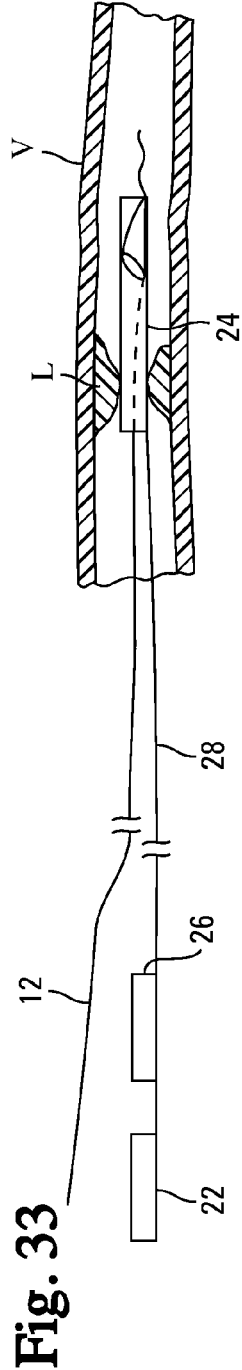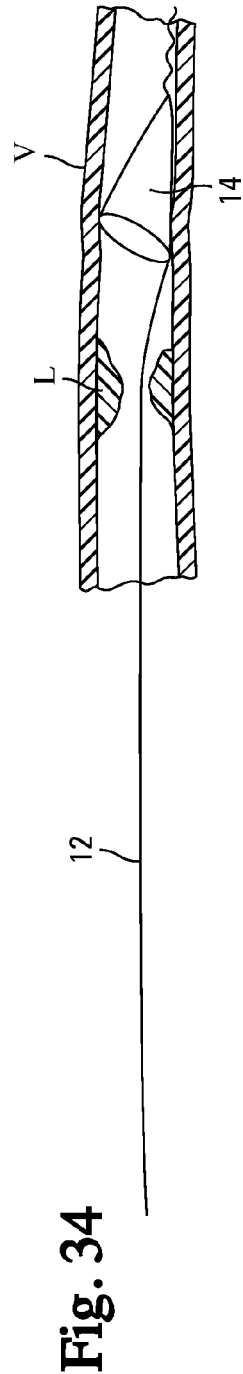

RAPID EXCHANGE CATHETERS FOR EMBOLIC PROTECTION DEVICES

This application claims the benefit of U.S. Provisional Application No. 60/837,378, filed Aug. 11, 2006, entitled "RX Catheters for Embolic Protection Devices", the contents of which are hereby incorporated by reference herein.

FIELD OF THE INVENTION

The present invention relates to embolic protection systems, and, more particularly, to delivery and recovery catheters for embolic protection devices.

BACKGROUND OF THE INVENTION

Vessels are commonly treated to reduce or eliminate narrowings caused by arteriosclerotic disease. Interventional treatments can include balloon angioplasty, stenting, drug eluting stenting, thrombectomy, atherectomy, and other procedures. During treatment particulate debris can be generated at the treatment site. Infarcts, strokes, and other major or minor adverse events are caused when debris embolizes into vasculature distal to the treatment site.

To prevent embolization of debris, embolic protection devices have been developed. During a procedure such devices can be placed distal to or proximal to the treatment site. Embolic protection devices can remove emboli from the bloodstream by filtering debris from blood, by occluding blood flow followed by aspiration of debris, or can cause blood flow reversal to effect removal of debris. The shape, length and other characteristics of an embolic protection device are typically chosen based on the anatomical characteristics in the vicinity of the treatment site.

Embolic protection devices are often delivered to and recovered from a treatment site in a patient's vessel by using catheters. In general, catheters in use can have a fixed wire (FW) configuration, an over-the-wire (OTW) configuration, or a rapid exchange (RX) configuration. FW configured catheters are used by pre-loading the embolic protection device into the catheter and advancing the assembly across a treatment site. While fewer steps are needed to use a fixed wire system they have larger crossing profiles and are less navigable than other systems through tortuous vessels. OTW configured catheters have a lumen that admits a wire therethrough and the lumen extends over substantially the entire length of the catheter. While OTW systems offer great support when trying to pass the catheter across tight lesions, the wire required must be more than twice as long as the catheter. OTW guidewires can be as long as 320 cm and it is cumbersome to handle wires of this length in a sterile field. RX configured catheters have a lumen that admits a wire therethrough but the lumen extends over a short distal length of the catheter. RX guidewires (typically 175 cm long) are easier and faster to use by one person, however RX systems do not offer the support offered by OTW systems.

In addition to the above issues discussed for FW, OTW, and RX catheters, some doctors prefer to have an option to sometimes cross a treatment site with a conventional guidewire before crossing the site with an embolic protection device. This alternate method allows a familiar guidewire, with characteristics appropriate for crossing a lesion or appropriate for support of subsequently inserted devices, to successfully cross a treatment site before opening the package of an embolic protection device. This approach avoids the cost of an embolic protection device in the event that the lesion cannot be crossed. Doctors also prefer to use certain guidewires due to their handling characteristics which are generally superior to those of the wire in an embolic protection device.

Accordingly, a need exists for an improved rapid exchange catheter for delivery and/or recovery of embolic protection devices.

SUMMARY OF THE INVENTION

The invention provides a catheter having a proximal portion and a distal portion, the catheter comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, and wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen.

The invention provides an assembly for delivering a catheter, the assembly comprising a guide wire and a catheter as described herein.

The invention provides an assembly comprising an embolic protection device and a catheter as described herein. In embodiments of the invention, the embolic protection device comprises a filter or an occlusive device.

The invention provides a method for positioning a catheter within a patient's blood vessel, the method comprising: providing a catheter, the catheter having a proximal portion and a distal portion, the catheter comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, and wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen, providing a guide wire having a proximal end and a distal end; advancing the guide wire to a target site within the patient's blood vessel; disposing the guide wire proximal end within the lumen of the first elongate tubular body; and advancing the catheter over the guide wire to the target site.

The invention provides a method for positioning a catheter within a patient's blood vessel, the method comprising: providing a catheter, the catheter having a proximal portion and a distal portion, the catheter comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, and wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen, and advancing the catheter to a target site within the patient's blood vessel using a guide catheter.

The invention provides an apparatus comprising a packaging system and a catheter as described herein, the packaging system comprising a packaging hoop and one or more clips.

The invention provides a catheter having a proximal portion and a distal portion, the catheter comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, and when the first and second elongate tubular bodies are adjacent to each other the lumens of the first and second elongate tubular bodies form one continuous lumen.

The invention provides a method for positioning a catheter within a patient's blood vessel, the method comprising: providing a catheter, the catheter having a proximal portion and a distal portion, the catheter comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, and when the first and second elongate tubular bodies are adjacent to each other the lumens of the first and second elongate tubular bodies form one continuous lumen; providing a guide wire having a proximal end and a distal end; advancing the guide wire to a target site within the patient's blood vessel; disposing the guide wire proximal end within the lumen of the first elongate tubular body; and advancing the catheter over the guide wire to the target site.

According to one aspect of the present invention, an embolic protection delivery and recovery catheter comprises a double ended catheter having a shuttle captive on the central portion of the catheter. One end of the catheter is comprised of an RX configuration and may be used for recovery of an embolic protection device. The opposite end of the catheter is also comprised of an RX configuration and may be used for delivery of an embolic protection device. The captive shuttle can slide along the length of the catheter between the two ends of the catheter. Means are provided to lock the shuttle to the delivery end of the catheter, and to releasably lock an embolic protection device within the shuttle. A packaging system is provided for the catheter and associated embolic protection device.

It is to be understood that that both the foregoing general description and the following detailed description are exemplary and explanatory and are intended to provide further explanation of the invention as claimed.

BRIEF DESCRIPTION OF THE DRAWINGS

The above and further advantages of the invention may be better understood by referring to the following description in conjunction with the accompanying drawings.

FIGS. 5 to 20 illustrate conceptually partial cross-sectional diagrams of portions of the embolic protection delivery and recovery catheter illustrated in FIG. 2.

FIGS. 21 and 22 illustrate conceptually partial isometric cross-sectional diagrams of portions of the embolic protection delivery and recovery catheter illustrated in FIG. 2.

FIGS. 32 to 34 illustrate conceptually schematic diagrams of an alternate method of using an embolic protection delivery and recovery catheter in accordance with the present invention.

DETAILED DESCRIPTION OF THE INVENTION

Figure 1:
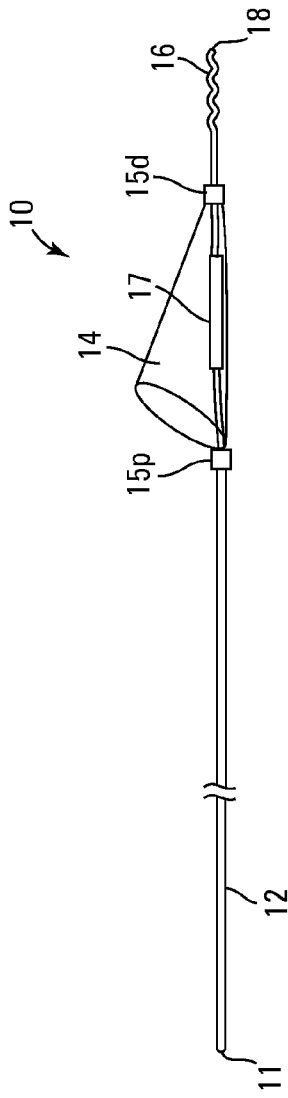
FIG. 1 illustrates conceptually a partial side view diagram of an embolic protection device.

The invention provides a catheter having a proximal portion and a distal portion, the catheter comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, and wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen. In one embodiment, no portion of the elongate member is in the lumen of the first elongate tubular body.

In one embodiment, the catheter further comprises a third elongate tubular body having a proximal portion, a distal portion, a proximal end, a distal end, and a lumen extending between the proximal end and the distal end, the third elongate tubular body being fixedly attached on the proximal portion of the elongate member, the third elongate tubular body being proximal of the second elongate tubular body. In an embodiment, the third elongate tubular body is tandem to the second elongate tubular body.

In one embodiment, the elongate member is cylindrical. In embodiments of the invention, the lumen of the first elongate tubular body has a constant diameter, the lumen of the second elongate tubular body has a constant diameter, and the lumens of the first and second elongate tubular bodies have the same constant diameter. In an embodiment, an outer diameter of the first elongate tubular body is constant.

The catheter can be an embolic protection device delivery catheter or an embolic protection device delivery and recovery catheter. In an embodiment, the first and second elongate tubular bodies are formed of one or more polymers.

In one embodiment, the first and second elongate tubular bodies are maintained in rotational alignment with each other by cooperating structures on the elongate member and on the second elongate tubular body. In an embodiment, the cooperating structures are a portion of the elongate member having a partial circular cross-section and a second lumen in the second elongate tubular body, the second lumen having a partial circular cross-section. In one embodiment, the portion of the elongate member having a partial circular cross-section extends over 20 to 180 degrees of arc.

In embodiments of the invention, the catheter has a longitudinal length of 100 to 240 cm or 175 to 200 cm. In embodiments of the invention, the first elongate tubular body has a longitudinal length of 5 to 30 cm, the second elongate tubular body has a longitudinal length of 5 to 20 cm, and the third elongate tubular body has a longitudinal length of 5 to 30 cm. In embodiments of the invention, the first elongate tubular body has an outer diameter of 0.7 to 2 mm, the second elongate tubular body has an outer diameter of 0.7 to 2 mm, and the third elongate tubular body has an outer diameter of 0.7 to 2 mm.

In one embodiment, the third elongate tubular body has a soft tip at the proximal end and the diameter of the lumen of the third elongate tubular body is reduced in the soft tip. In an embodiment, the first elongate tubular body has a soft tip at the distal end.

In one embodiment, the locking mechanism comprises a finger that passes into a window on the elongate member when the second elongate tubular body and the first elongate tubular body are adjacent to each other. In an embodiment, the second elongate tubular body comprises a window that is centered over the window of the elongate member when the second elongate tubular body and the first elongate tubular body are adjacent to each other. In one embodiment, the finger is connected to a spring that blocks a portion of the lumen of the second elongate tubular body when the finger does not pass into the window on the elongate member. In one embodiment, the spring does not block a portion of the lumen of the second elongate tubular body when the finger passes into the window on the elongate member. In another embodiment, the second elongate tubular body comprises a window that is centered over the window of the elongate member when the second elongate tubular body and the first elongate tubular body are adjacent to each other, and wherein the spring does not block a portion of the lumen of the second elongate tubular body when the finger passes through the window on the elongate member and into the window of the second elongate tubular body.

The invention provides an assembly for delivering a catheter, the assembly comprising a guide wire and a catheter as described herein.

The invention provides an assembly comprising an embolic protection device and a catheter as described herein. In embodiments of the invention, the embolic protection device comprises a filter or an occlusive device.

The invention provides a method for positioning a catheter within a patient's blood vessel, the method comprising: providing a catheter, the catheter having a proximal portion and a distal portion, the catheter comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, and wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen, providing a guide wire having a proximal end and a distal end; advancing the guide wire to a target site within the patient's blood vessel; disposing the guide wire proximal end within the lumen of the first elongate tubular body; and advancing the catheter over the guide wire to the target site. In an embodiment, the guide wire is removed from the catheter after the catheter has been advanced to the target site. In an embodiment, an embolic protection device comprising a host wire is loaded into the lumen of the second elongate tubular body. In another embodiment, an embolic protection device comprising a host wire is loaded into the lumen of the second elongate tubular body, the locking mechanism being in the open configuration. In one embodiment, the embolic protection device is retained in the lumen of the second elongate tubular body and does not move relative to the second elongate tubular body as a distal end of the embolic protection device is advanced distally a portion of the distance to the target site by advancing the host wire distally. In an embodiment, the distal end of the second elongate tubular body is advanced by advancing the host wire distally so that the distal end of the second elongate tubular body is adjacent to the proximal end of the first elongate tubular body and the first elongate tubular body and the first and second elongate tubular bodies are locked together by the locking mechanism. In one embodiment, the distal end of the embolic protection device is advanced distally by advancing the host wire distally and a portion of the embolic protection device exits the distal end of the first elongate tubular body. In an embodiment, the catheter is removed from the target site while the embolic protection device remains at the target site. In an embodiment, a medical procedure is performed at the target site. In an embodiment, the embolic protection device is retrieved by reversing the orientation of the catheter so that the proximal portion of the catheter is closer to the target site than the distal portion of the catheter, and distally advancing the third elongate tubular body over the embolic protection device, and then removing the catheter and the embolic protection device.

The invention provides a method for positioning a catheter within a patient's blood vessel, the method comprising: providing a catheter, the catheter having a proximal portion and a distal portion, the catheter comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, and wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen, and advancing the catheter to a target site within the patient's blood vessel using a guide catheter. In an embodiment, an embolic protection device comprising a host wire is loaded into the lumen of the first elongate tubular body, the locking mechanism being in the open configuration. In one embodiment, the embolic protection device is retained in the lumen of the first elongate tubular body as a distal end of the embolic protection device is advanced distally to the target site. In an embodiment, the distal end of the embolic protection device is advanced distally by advancing the embolic protection device and a portion of the embolic protection device exits the distal end of the first elongate tubular body. In one embodiment, the catheter is removed from the target site while the embolic protection device remains at the target site.

The invention provides an apparatus comprising a packaging system and a catheter as described herein, the packaging system comprising a packaging hoop and one or more clips.

The invention provides a catheter having a proximal portion and a distal portion, the catheter comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, and when the first and second elongate tubular bodies are adjacent to each other the lumens of the first and second elongate tubular bodies form one continuous lumen.

The invention provides a method for positioning a catheter within a patient's blood vessel, the method comprising: providing a catheter, the catheter having a proximal portion and a distal portion, the catheter comprising: a first elongate tubular body having a proximal portion, a distal portion, a proximal end, a distal end, and a lumen extending between the proximal end and the distal end; a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, and when the first and second elongate tubular bodies are adjacent to each other the lumens of the first and second elongate tubular bodies form one continuous lumen; providing a guide wire having a proximal end and a distal end; advancing the guide wire to a target site within the patient's blood vessel; disposing the guide wire proximal end within the lumen of the first elongate tubular body; and advancing the catheter over the guide wire to the target site. In an embodiment, the guide wire is removed from the catheter after the catheter has been advanced to the target site. In an embodiment, an embolic protection device comprising a host wire is loaded into the lumen of the second elongate tubular body. In one embodiment, the embolic protection device is retained in the lumen of the second elongate tubular body and does not move relative to the second elongate tubular body as a distal end of the embolic protection device is advanced distally a portion of the distance to the target site by advancing the host wire distally. In an embodiment, the distal end of the second elongate tubular body is advanced by advancing the host wire distally so that the distal end of the second elongate tubular body is adjacent to the proximal end of the first elongate tubular body. In one embodiment, the distal end of the embolic protection device is advanced distally by advancing the host wire distally and a portion of the embolic protection device exits the distal end of the first elongate tubular body. In an embodiment, the catheter is removed from the target site while the embolic protection device remains at the target site. In an embodiment, a medical procedure is performed at the target site. In an embodiment, the embolic protection device is retrieved by reversing the orientation of the catheter so that the proximal portion of the catheter is closer to the target site than the distal portion of the catheter, and distally advancing the third elongate tubular body over the embolic protection device, and then removing the catheter and the embolic protection device.

FIG. 1 illustrates an exemplary prior art embolic protection device suitable for use with the present invention. Embolic protection device 10 is comprised of host wire 12 having proximal end 11, distal end 18, and floppy tip 16. Proximal end of filter basket 14 is attached to proximal band 15p and distal end of filter basket 14 is attached to distal band 15d. Proximal band 15p and distal band 15d are slideably mounted on host wire 12. Stop 17 is attached to host wire 12 and limits travel of slideably mounted bands 15p and 15d. While FIG. 1 illustrates a distal embolic protection filter, it is to be understood that other types of embolic protection devices may be used with the present invention including but not limited to distal occlusive devices and proximal occlusive devices.

For example, an embolic protection system comprised of an occlusive device on a host wire can be used with the present invention. The occlusive device can be an inflatable balloon, a mesh covered by a membrane, or other structures and can be actively expanded, such as by expanding a balloon, or can be self-expanding. The occlusive device must remain in position when deployed and resist forces caused by flow in a vessel and may comprise anchors on the surface of the occlusive device such as barbs, hooks, surface roughness, or other anchoring geometries as are known in the art. In one embodiment, the occlusive device is a self-expanding, laser cut, open mesh nitinol tube covered with a thin membrane of silicone polymer and a retractable sheath comprised of a catheter is positioned over the occlusive device so as to constrain the occlusive device during delivery to a vessel. In one embodiment, the occlusive device is an inflatable balloon and the host wire comprises an inflation lumen. The inflatable balloon may be comprised of polyethylene, polyester, nylon, polyether block amide such as PEBAX®, silicone, latex, urethane, or other materials as are known in the art and may be inflated using saline, radiographic contrast media, mixtures of saline and radiographic contrast media, $CO_2$, or other fluids as are known in the art. In one embodiment, the occlusive device is a nylon twelve balloon and is inflated using $CO_2$. In use, after the occlusive embolic protection device has been deployed and emboli have been generated, aspiration is applied through a separate catheter or through an aspiration lumen in the occlusive device to aspirate emboli out of the body from the vicinity of the treatment site.

In yet another non-limiting example, an embolic protection system incorporating flow reversal techniques can be used with the present invention. In an example of such a system, an occlusive device having an aspiration lumen and a working lumen is expanded proximal to a treatment site. After expansion of the occlusive device, suction can be applied to the proximal end of the aspiration lumen to cause blood to flow from the treatment site retrograde through the aspiration lumen. The interventional procedure can then be performed through the working lumen and any emboli generated during the procedure will be transported by the retrograde flow proximally from the treatment site until removed from the body.

Figure 2:
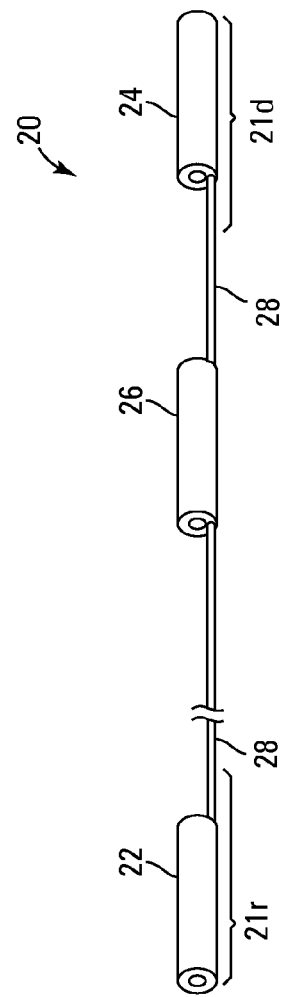
FIG. 2 illustrates conceptually an isometric partial side view diagram of an embolic protection delivery and recovery catheter in accordance with the present invention.

FIG. 2 illustrates an embolic protection delivery and recovery catheter in accordance with the present invention. Embolic protection delivery and recovery catheter 20 has delivery end 21d and recovery end 21r. Delivery catheter 24 and recovery catheter 22 are fixedly attached to delivery and recovery ends of track 28 respectively. Shuttle 26 is slideably coupled to track 28 and can slide along a portion of track 28 between delivery catheter 24 and recovery catheter 22. Shuttle 26 is captive on track 28 in that fixed attachment of delivery catheter 24 and recovery catheter 22 to track 28 prevents shuttle 26 from sliding off of either end of track 28. Track 28 provides adequate stiffness to allow ends of catheter 20 to be advanced to a region of interest in a conduit in a patient, such as to the vicinity of a stenosis in an artery of a patient. Track 28 is comprised of metal such as stainless steel, ELGILOY®, nitinol; engineering polymer such as polyetheretherketone (PEEK), polyimide, liquid crystal polymer (LCP), nylon, polyester, braid-reinforced polymer, or other metals, polymers, or materials as are known in the art. Track 28 maintains slideable shuttle 26 in rotational alignment with delivery catheter 24 by means of cooperating structures on each of track 28 and shuttle 26 such as a non-circular cross-section track 28 with non-circular cooperating lumen in shuttle 26, one or more mating key and keyway, or other structure.

In some embodiments, catheter 20 has an overall length of 100 to 240 cm, delivery catheter 24 has a length of 5 to 30 cm, recovery catheter 22 has a length of 5 to 30 cm, and shuttle 26 has a length of 5 to 20 cm. In one embodiment, catheter 20 has an overall length of 175 to 200 cm. In one embodiment, delivery catheter 24 has a length of 5 to 25 cm. In another embodiment, delivery catheter 24 has a length of 5 to 18 cm, and in another embodiment delivery catheter 24 has a length of 5 to 9 cm. In one embodiment, recovery catheter 22 has a length of 5 to 25 cm. In another embodiment, recovery catheter 22 has a length of 5 to 18 cm, and in another embodiment recovery catheter 22 has a length of 5 to 9 cm. In one embodiment, shuttle 26 has a length of 5 to 15 cm. In another embodiment, shuttle 26 has a length of 5 to 12 cm, and in another embodiment shuttle 26 has a length of 5 to 9 cm.

In some embodiments, delivery catheter 24 has an outer diameter of 2 to 6 Fr (0.7 to 2 mm), recovery catheter 22 has an outer diameter of 2 to 7 Fr (0.7 to 2.3 mm), and shuttle 26 has an outer diameter of 2 to 6 Fr (0.7 to 2 mm). In one embodiment, delivery catheter 24 has an outer diameter of 2 to 4 Fr (0.7 to 1.3 mm). In another embodiment, delivery catheter 24 has an outer diameter of 2 to 3 Fr (0.7 to 1 mm), and in another embodiment delivery catheter 24 has an outer diameter of 2 to 2.5 Fr (0.7 to 0.85 mm). In one embodiment, recovery catheter 22 has an outer diameter of 2 to 5 Fr (0.7 to 1.7 mm). In another embodiment, recovery catheter 22 has an outer diameter of 2 to 4 Fr (0.7 to 1.3 mm), and in another embodiment recovery catheter 22 has an outer diameter of 2 to 3 Fr (0.7 to 1 mm). In one embodiment, shuttle 26 has an outer diameter of 2 to 4 Fr (0.7 to 1.3 mm). In another embodiment, shuttle 26 has an outer diameter of 2 to 3 Fr (0.7 to 1 mm), and in another embodiment shuttle 26 has an outer diameter of 2 of 2.5 Fr (0.7 to 0.85 mm).

Figure 3:
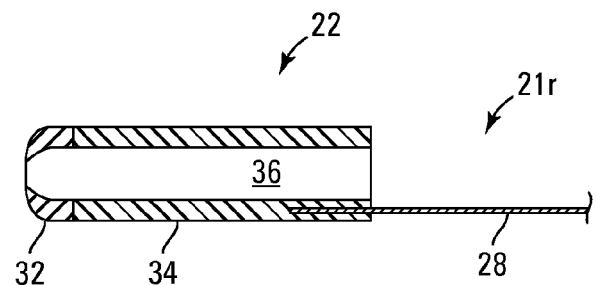
FIGS. 3 and 4 illustrate conceptually partial cross-sectional diagrams of portions of the embolic protection delivery and recovery catheter illustrated in FIG. 2.

FIG. 3 illustrates a portion of the embolic protection delivery and recovery catheter illustrated in FIG. 2. Recovery catheter 22 is comprised of tubing 34 and soft tip 32 and has lumen 36 passing therethrough. Tubing is made of polymer including but not limited to polyether block amide such as PEBAX®, polyethylene, nylon, polyester, and other materials known in the art, and may be made by processes known by those skilled in the art, such as extrusion. In some embodiments catheter 22 is torqueable and comprises metal reinforcement, for example braided wire. Soft tip 32 is made of polymers including but not limited to polyether block amide such as PEBAX®, polyurethane, nylon, silicone, and other materials known in the art, and may be made by processes known by those skilled in the art, such as extrusion or molding. Soft tip 32 may be comprised of radiopaque materials such as barium sulphate, bismuth subcarbonate, tungsten, bismuth oxychloride, or other known materials. In another embodiment, one or more marker bands (not shown) may be incorporated into the distal region of catheter 22 using materials and methods such as those described in connection with FIG. 4.

Soft tip 32 may have a shape such as a tapered wall thickness that facilitates advancement across patient lumen surface irregularities such as calcification, poorly apposed implanted stents, or other surface irregularity. One such tip structure is described in U.S. Pat. No. 6,979,343 B2, incorporated by reference in its entirety herein. In another embodiment, the axis of the distal 5 to 15 mm of recovery catheter 22 is bent 5 to 30 degrees relative to the axis of the proximal portion of recovery catheter 22 so that the catheter can be advanced across lumenal surface irregularities by rotating the catheter tip when resistance to advancement is encountered. In yet another embodiment, distal portion of catheter 22 is shapeable such that the distal portion can be bent by the operator, and to facilitate bending malleable polymers or malleable metallic reinforcements (not shown) are incorporated into the distal region of catheter 22. Soft tip 32 is permanently attached to tubing 34 by a process such as thermal fusing, welding, insert molding, adhesives, solvent welding, or other processes as are known in the art. Tubing 34 is attached to track 28 by processes such as thermal fusing, welding, insert molding, adhesives, or other processes as are known in the art.

Figure 4:
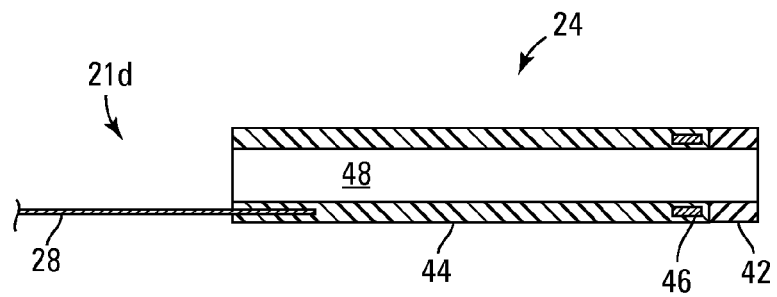

FIG. 4 illustrates a portion of the embolic protection delivery and recovery catheter illustrated in FIG. 2. Delivery catheter 24 is comprised of tubing 44, soft tip 42, and radiopaque marker 46, and has lumen 48 passing therethrough. Tubing is made of polymer including but not limited to polyether block amide such as PEBAX®, polyethylene, nylon, polyester, and other materials known in the art, and may be made by processes known by those skilled in the art, such as extrusion. Soft tip 42 is made of polymers including but not limited to polyether block amide such as PEBAX®, polyurethane, nylon, silicone, and other materials known in the art, and may be made by processes known by those skilled in the art, such as extrusion or molding. Radiopaque marker 46 is made of platinum or platinum alloy, gold, tungsten, tantalum, or other materials as known in the art. Radiopaque marker 46 may be positioned on catheter 24 at any position relative to the wall thickness of catheter 24 and may be fused, crimped, swaged, heat bonded, adhesively bonded, or otherwise attached to catheter 24. In an alternative embodiment, soft tip 42 is comprised of radiopaque materials and made using methods such as those described in connection with FIG. 3.

Soft tip 42 may have a shape such as a tapered wall thickness that facilitates advancement across patient lumen surface irregularities such as calcification, poorly apposed implanted stents, or other surface irregularity. One such tip structure is described in U.S. Pat. No. 6,979,343 B2, incorporated by reference in its entirety herein. Soft tip 42 is permanently attached to tubing 44 by a process such as thermal fusing, welding, insert molding, adhesives, solvent welding, or other processes as are known in the art. Tubing 44 is attached to track 28 by processes such as thermal fusing, welding, insert molding, adhesives, or other processes as are known in the art.

FIGS. 5 to 20 illustrate portions of the embolic protection delivery and recovery catheter illustrated in FIG. 2. As illustrated in FIGS. 5 to 7, shuttle 26 is comprised of shell 50 and insert 70 and is shown positioned along track 28. Exemplary embolic protection device 10 (mesh 14 not shown) is shown within lumen 27 of shuttle 26. Shuttle finger 71 is shown in a position which allows the filter to pass distally through shuttle lumen 27 and delivery catheter lumen 48 and which locks shuttle 26 in fixed axial relationship with delivery catheter 24. Shuttle finger 71 extends into track window 28w and into shell window 50w as discussed in greater detail below.

Figure 8:
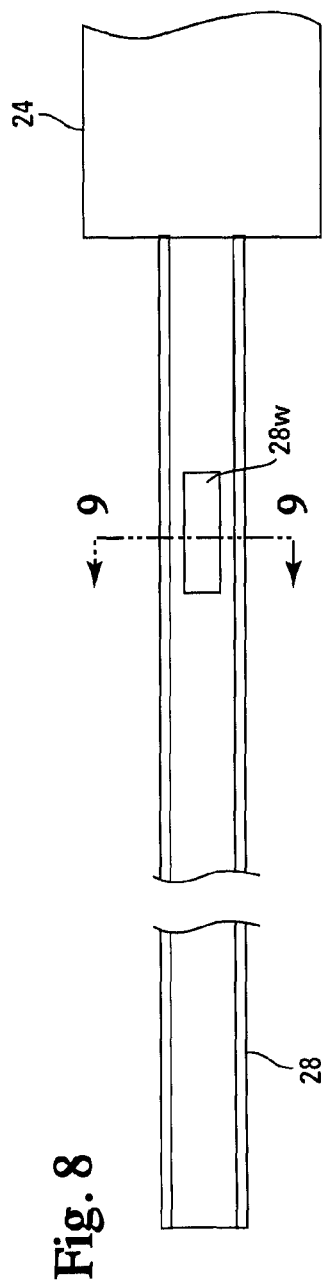
Figure 9:
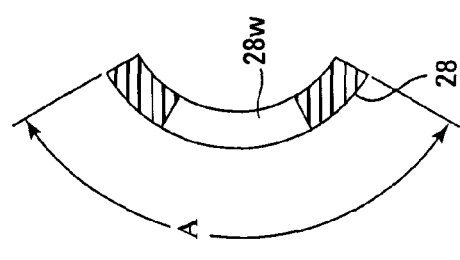
Figure 10:
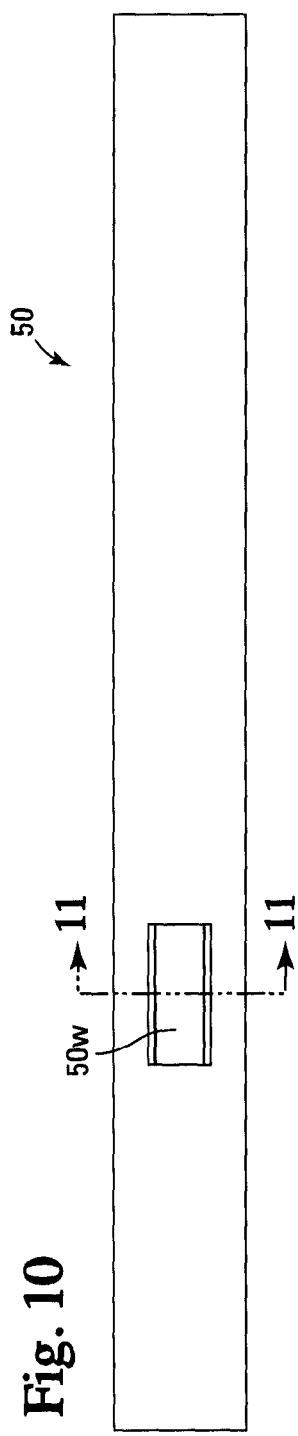
Figure 12:
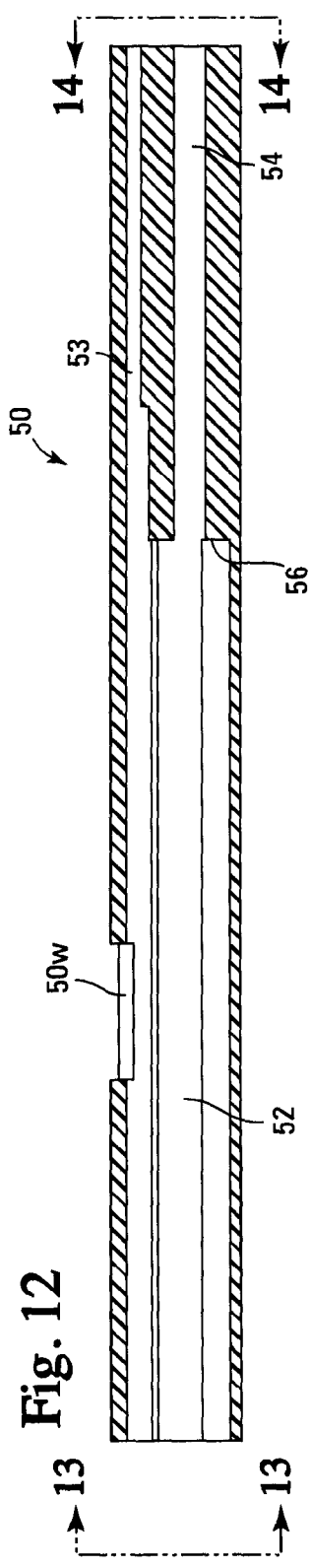
Figure 14:
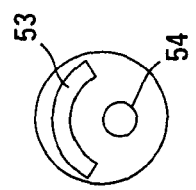
Figure 13:
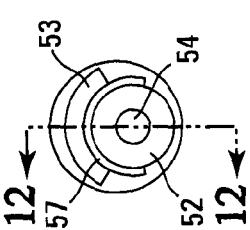
Figure 11:
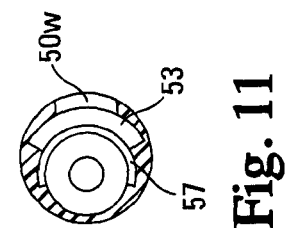

FIGS. 8 and 9 illustrate track 28 having window 28w positioned proximally to delivery catheter 24. Track window 28w is dimensioned to freely pass finger 71 into window 28w and can be fabricated by laser cutting, etching, drilling, or other means. In the embodiment shown, track 28 has an arcuate cross-sectional shape and can be made, for example, by sectioning a tube by grinding, or by forming a flat strip into an arcuate shape by stamping. In one embodiment, track 28 is comprised of nitinol for superior kink resistance, especially in the vicinity of track window 28w. In some embodiments, track 28 has a cross-sectional shape extending over 20 to 180 degrees of arc A. In another embodiment track 28 has a cross-sectional shape extending over 45 to 120 degrees of arc A, and in another embodiment track 28 has a cross-sectional shape extending over 60 to 90 degrees of arc A.

FIGS. 10 to 14 illustrate shuttle shell 50 having shell window 50w, lumen 52, track lumen 53, host wire lumen 54, and distally facing stop surface 56. Shell 50 is comprised of polymer including but not limited to polyether block amide such as PEBAX®, polyethylene, nylon, polyester, and other materials known in the art, and may be made by processes known by those skilled in the art, such as extrusion. Shell window 50w is dimensioned to freely pass finger 71 into window 50w and can be fabricated by laser cutting, molding, drilling, cutting, or other means. Lumen 52 has pocket 57 which is dimensioned to allow insert 70 to be inserted therein and bonded to shell 50. Lumen 52 with insert 70 assembled therein is dimensioned to freely slidingly accept embolic protection device 10 therein. Track lumen 53 is dimensioned to slidingly accept track 28 therein and to maintain rotational orientation of shuttle 26 relative to delivery catheter 24 (to which track 28 is rotationally fixedly attached). Host wire lumen 54 is dimensioned to slidingly accept host wire 12 of embolic protection device 10. Distally facing stop surface 56 is at the junction of lumen 52 and host wire lumen 54. Distally facing stop surface 56 prevents movement of embolic protection device 10 proximal band 15p in a direction proximal to distally facing stop surface 56.

FIGS. 15 to 20 illustrate insert 70 having insert body 72, spring 74, finger 71, and optional reflow holes 76. Insert 70 is comprised of metal such as stainless steel, ELGILOY®, nitinol; engineering polymer such as PEEK, polyimide, liquid crystal polymer, nylon, polyester, braid-reinforced polymer, or other metals, polymers, or materials as are known in the art. Insert body 72 may be generally cylindrical in overall shape and is dimensioned to nest into shell 50. In one embodiment, insert body 72 has a generally arcuate shape as illustrated in FIGS. 16 to 18. Spring 74 may be integral with insert body 72 as shown in FIG. 15 and may be fabricated by cutting slots in insert body 72 using methods such as laser cutting. Similarly, finger 71 may be integral with spring 74 as shown in FIGS. 15 and 20 and may be fabricated by cutting slots in spring 74 using methods such as laser cutting. One or more optional reflow holes 76 are cut or drilled into insert body 72 to provide additional means by which insert 70 may be permanently attached to shell 50. In one example, shell 50 is partially melted to cause material of shell 50 to flow into reflow holes 76 and then shell 50 is allowed to solidify. Finger 71 is oriented out of plane with spring 74 as illustrated in FIG. 20. In one embodiment insert 70 is comprised of stainless steel and finger 71 is bent out of plane with spring 74. In another embodiment, insert 70 is comprised of nitinol and finger 71 is heat set while constrained out of plane with spring 74.

FIGS. 21 and 22 illustrate portions of the embolic protection delivery and recovery catheter illustrated in FIG. 2 in different functional positions. FIG. 21 illustrates exemplary embolic protection device 10 (mesh 14 not shown) locked in shuttle 26 and FIG. 22 shows embolic protection device 10 (mesh 14 not shown) unlocked in shuttle 26. In FIG. 21, track window 28w and shell window 50w are not aligned over one another, and finger 71 is depressed towards axis of lumen 27, causing spring end 74e to protrude into lumen 27. Distal marker band 15d of embolic protection device 10 is thereby prevented from traveling distally within lumen 27 of shuttle 26. Additionally, proximal marker band 15p of embolic protection device 10 is prevented from traveling proximally within lumen 27 of shuttle 26 by stop surface 56 (shown in FIG. 12). Therefore, in the functional position illustrated in FIG. 21, embolic protection device 10 is held captive within shuttle 26, and axial motion of host wire 12 can move shuttle 26 distally or proximally along track 28.

In FIG. 22, track window 28w and shell window 50w are aligned over one another, and finger 71 is within track window 28w and shell window 50w, allowing spring 74 to retract spring end 74e out of lumen 27. Distal marker band 15d of embolic protection device 10 is thereby allowed to travel distally within lumen 27 of shuttle 26. Additionally, proximal marker band 15p of embolic protection device 10 is prevented from traveling proximally within lumen 27 of shuttle 26 by stop surface 56 (shown in FIG. 12). Further, shuttle 26 is prevented from sliding proximally along track 28 due to presence of finger 71 within track 28 and in one embodiment distal end of shuttle 26 abuts proximal end of delivery catheter 24 (shown in FIG. 5). Therefore, in the functional position illustrated in FIG. 22, shuttle 26 is locked to delivery catheter 24, embolic protection device 10 can be advanced through lumen 27 of shuttle 26 and through lumen 48 of delivery catheter 24, and axial motion of host wire 12 cannot move shuttle 26 distally or proximally along track 28.

Figure 23:
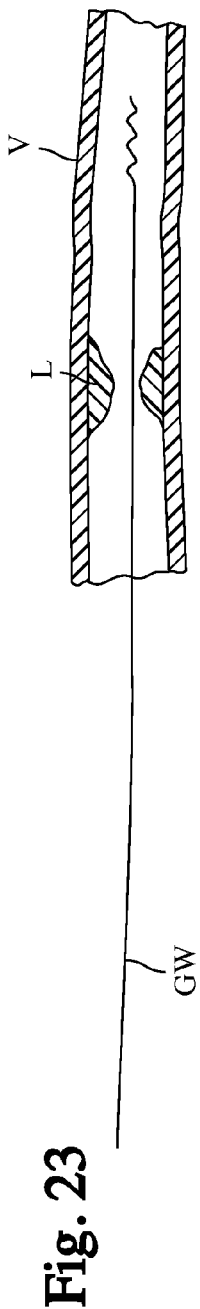
FIGS. 23 to 31 illustrate conceptually schematic diagrams of a method of using an embolic protection delivery and recovery catheter in accordance with the present invention.
Figure 24:
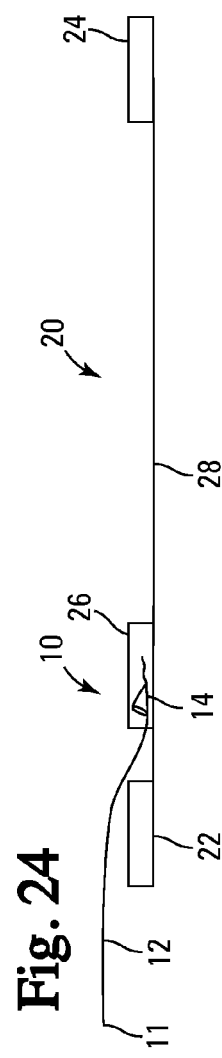

FIGS. 23 to 31 illustrate an exemplary method of using an embolic protection delivery and recovery catheter with a preferred guidewire in accordance with the present invention. Guide catheter or sheath (not shown) is used to access a vessel in a patient using methods known in the art. A guidewire GW is chosen based on evaluation of a lesion L in a vessel V and the guidewire is advanced through the guide or sheath and across the lesion as illustrated in FIG. 23. Separately, proximal end 11 of host wire 12 of embolic protection device 10 is backloaded through lumen of shuttle 26 and filter 14 is drawn into lumen of shuttle 26 by drawing host wire 12 proximally (FIG. 24) until proximal marker band 15p abuts stop surface 56 and distal marker band 15d is proximal to spring end 74e, thereby locking embolic protection device 10 into shuttle 26. Shuttle 26 is drawn proximally along track 28 to a position near recovery catheter 22.

Figure 25:
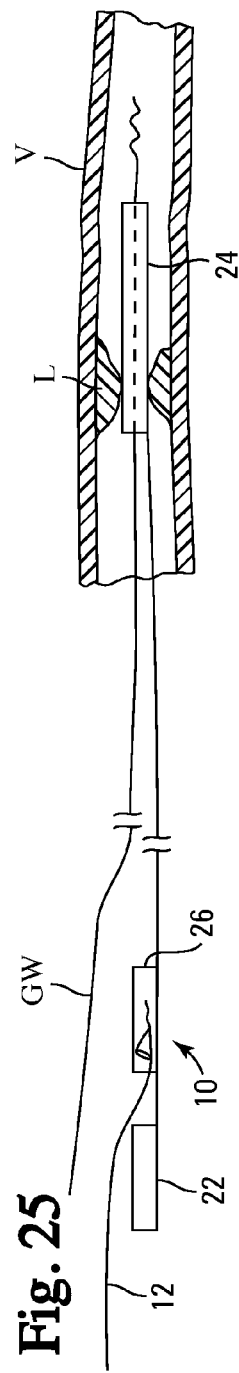
Figure 26:
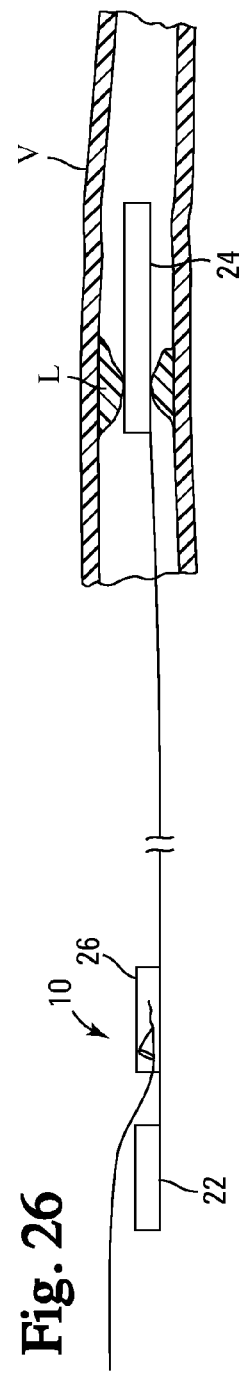

Proximal end of guidewire GW is backloaded through lumen of delivery catheter 24 and while holding guidewire GW in a steady axial location, track 28 is pushed distally to advance delivery catheter 24 along guidewire GW through vessel V and across lesion L (FIG. 25). Guidewire GW is then withdrawn from the vessel (FIG. 26).

Figure 27:
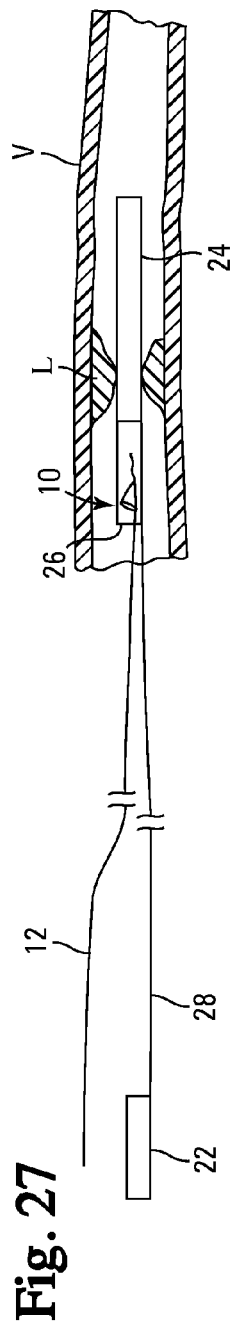
Figure 28:
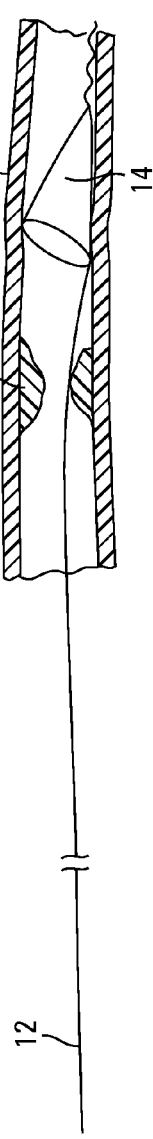
Figure 29:
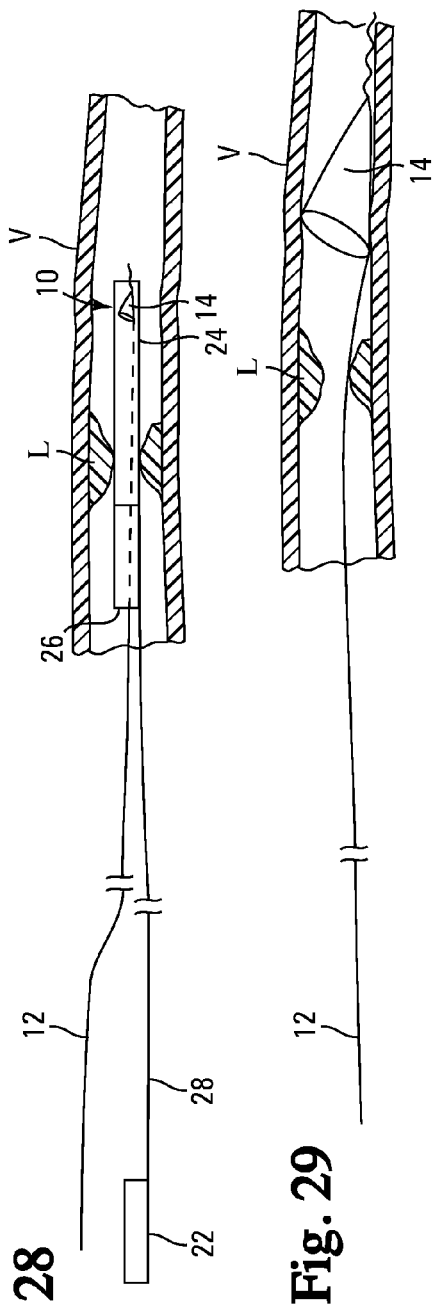

Next, host wire 12 is advanced distally, causing shuttle 26 to advance distally along track 28 until distal end of shuttle 26 contacts proximal end of delivery catheter 24 at which point track window 28w and shell window 50w align, allowing finger 71 to enter windows 28w and 50w, thereby removing spring end 74e from lumen 27 and locking shuttle to track 28 in a position immediately proximal to delivery catheter 24 (FIG. 27). Continued distal advancement of host wire 12 advances filter 14 into and through lumen of delivery catheter 24 until filter 14 is located immediately proximal to distal end of delivery catheter (FIG. 28), distal to lesion L, and at the desired deployment location in vessel V. When the above criteria are met, host wire 12 is axially immobilized and track 28 is moved proximally to uncover and deploy filter in vessel V. Embolic protection delivery and recovery catheter 20 is then removed from the body (FIG. 29).

Figure 30:
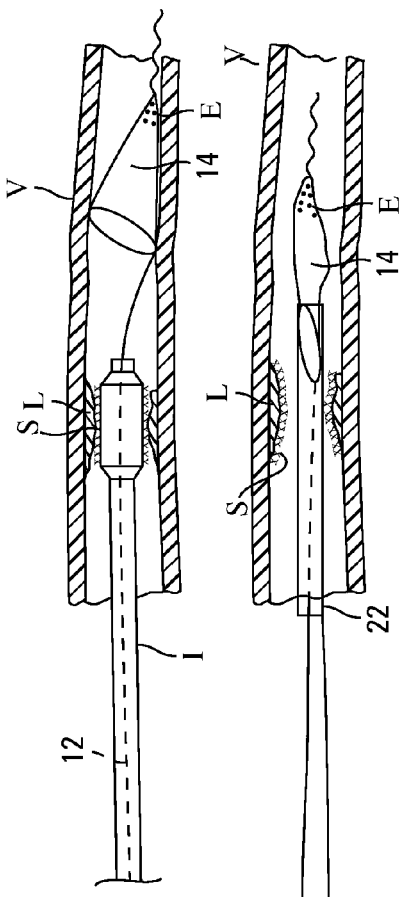
Figure 31:
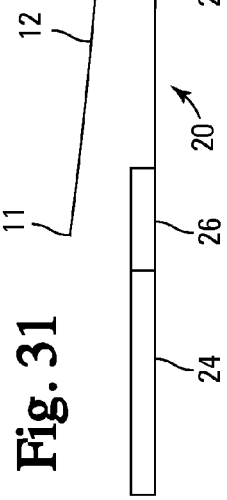
Figure 35:
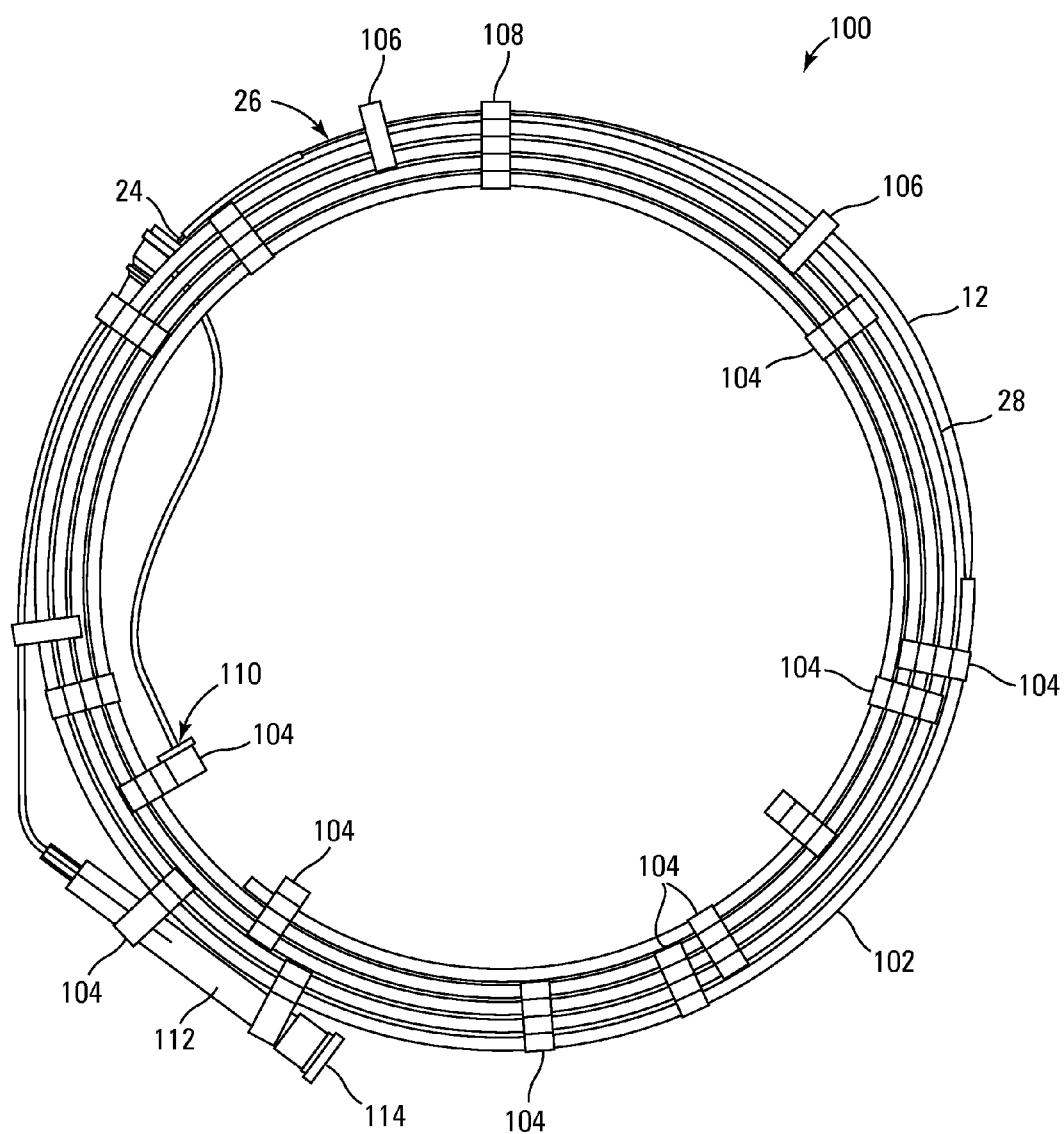
FIGS. 35 to 39 illustrate conceptually partial side view or cross-sectional diagrams of a packaging system for the embolic protection delivery and recovery catheter illustrated in FIG. 2.

Interventional devices I, such as angioplasty catheters, stent delivery systems, atherectomy devices, thrombectomy devices, ultrasound catheters, and the like may be advanced to the vicinity of lesion L by tracking them along host wire 12. Stents S or other implants may be deployed in the vicinity of lesion L. Embolic debris E generated, if any, will flow distally and be captured by filter 14 (FIG. 30).

Embolic protection delivery and recovery catheter 20 is then advanced into vessel V by backloading proximal end 11 of host wire 12 into distal end of recovery catheter 22 and then pushing track 28 distally to advance recovery catheter 22 along host wire 12 to the vicinity of filter 14. Recovery catheter 22 is advanced over at least the opening of filter 14 (FIG. 31) and the recovery catheter 22, host wire 12, and filter 14 are withdrawn from the patient's vessel V as a combined unit.

FIGS. 32 to 34 illustrate another exemplary method of using embolic protection delivery and recovery catheter 20 as a fixed wire system in accordance with the present invention. Guide catheter or sheath (not shown) is used to access a vessel in a patient using methods known in the art. Proximal end 11 of host wire 12 of embolic protection device 10 is backloaded through lumen of delivery catheter 24 and filter 14 is drawn into lumen of delivery catheter 24 by drawing host wire 12 proximally until filter is located immediately proximal to distal end of delivery catheter and tip of host wire extends distally of delivery catheter 24 (FIG. 32).

Embolic protection device 10 and delivery catheter 24 are then advanced as a unit through guide catheter or sheath, into vessel V and past lesion L by holding track 28 and host wire 12 in fixed axial relationship and advancing them distally until filter 14 is at the desired deployment location in vessel V (FIG. 33). When the above criteria are met, host wire 12 is axially immobilized and track 28 is moved proximally to uncover and deploy filter in vessel V. Embolic protection delivery and recovery catheter 20 is then removed from the body (FIG. 34).

Interventional devices such as angioplasty catheters, stent delivery systems, atherectomy devices, thrombectomy devices, ultrasound catheters, and the like may be advanced to the vicinity of lesion L by tracking them along host wire 12. Stents S or other implants may be deployed in the vicinity of lesion L. Embolic debris E generated, if any, will flow distally and be captured by filter 14 (FIG. 30).

Embolic protection delivery and recovery catheter 20 is then advanced into vessel V by backloading proximal end 11 of host wire 12 into distal end of recovery catheter 22 and then pushing track 28 distally to advance recovery catheter 22 along host wire 12 to the vicinity of filter 14. Recovery catheter 22 is advanced over at least the opening of filter 14 (FIG. 31) and the recovery catheter 22, host wire 12, and filter 14 are withdrawn from the patient's vessel V as a combined unit.

FIGS. 35 to 39 illustrate a packaging system for the embolic protection delivery and recovery catheter 20 illustrated in FIG. 2. Packaging system 100 is comprised of packaging hoop 102, clips 104, clip 106, flush port 110, flushing chamber 112, and one-way check valve 114. Packaging hoop 102 may be comprised of polyethylene tubing and houses both embolic protection delivery and recovery catheter 20 and embolic protection device 10 therein, and has shuttle 26 extending therefrom. Clips 104 are comprised of polymer and snap onto packaging system components so as to maintain the configuration illustrated in FIG. 35. Clip 106 is comprised of polymer and snaps onto embolic protection delivery and recovery catheter 20 and/or embolic protection device 10 components so as to maintain the configuration illustrated in FIG. 35. Flush port 110 may be comprised of a luer fitting and is connected to a standard syringe (not shown) during preparation of the embolic protection delivery and recovery catheter 20 and/or embolic protection device 10 before introducing these systems into a patient. Flushing chamber 112 and one-way check valve 114 may be commonly available components and are used to collect flushing fluid during preparation of the embolic protection delivery and recovery catheter 20 and/or embolic protection device 10. Filter 14 of embolic protection device 10 is housed within flush chamber 112.

Figure 36:
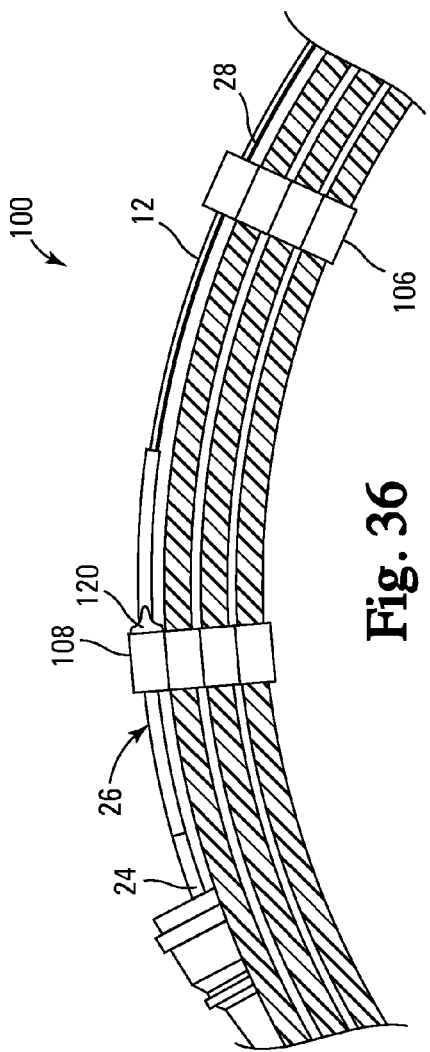
Figure 37:
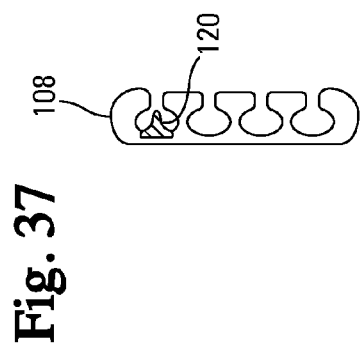
Figure 38:
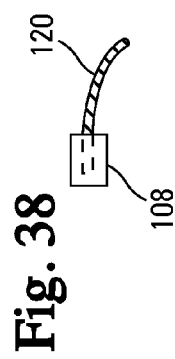
Figure 39:
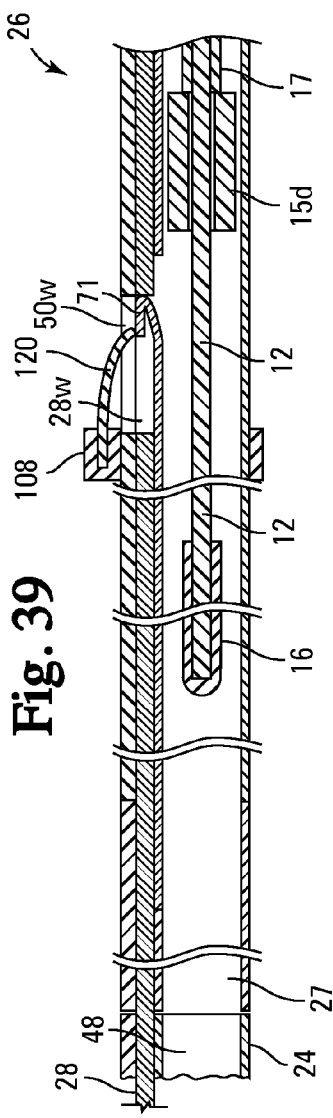

FIGS. 36 to 38 illustrate portions of packaging system 100 in greater detail. Delivery catheter 24 and shuttle 26 are locked together by finger 71 by sliding them into contact with one another. Track wire 28 and host wire 12 are secured in position by clip 106. Shuttle 26 is secured in position by clip 108 having release finger 120 positioned over shell window 50w (not shown). Release finger 120 extends through shell window 50w and track window 28w and is in contact with finger 71 (FIG. 39). Release finger 120 is comprised of spring temper material such as ELGILOY® or stainless steel, super-elastic nitinol, or other materials known in the art.

One exemplary method of preparing embolic protection delivery and recovery catheter 20 and embolic protection device 10 for use in a patient is as follows. Flush port 110 is unclipped from clip 104, a syringe filled with sterile saline is connected to flush port 110 and the saline is injected into the packaging system while orienting one-way valve 114 higher than flush chamber 112. Saline collects in flush chamber 112 where it will displace air from filter 14 and chamber 112 through valve 114. One-way valve 114 will prevent entry of air back into flush chamber 112 when chamber orientation is changed after air is displaced. Host wire 12 is removed from clip 106 and drawn proximally until proximal band 15p abuts stop surface 56, thereby drawing filter into delivery catheter 24 and shuttle 26. Track 28 is removed from clip 106 and drawn proximally while simultaneously depressing release finger 120 against finger 71, thereby unlocking shuttle 26 from delivery catheter 24 and allowing shuttle 26 to move proximally along track 28. Embolic protection delivery and recovery catheter 20 and embolic protection device 10 are next removed from packaging system 100 and can be used in a patient.

While this document has described an invention mainly in relation to embolic protection of vessels, it is envisioned that the invention can be applied to other conduits in the body as well including arteries, veins, bronchi, ducts, ureters, urethra, and other lumens intended for the passage of air, fluids, or solids.

While the various embodiments of the present invention have related to embolic protection systems, the scope of the present invention is not so limited. Further, while choices for materials and configurations may have been described above with respect to certain embodiments, one of ordinary skill in the art will understand that the materials described and configurations are applicable across the embodiments.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A catheter having a proximal portion and a distal portion, the catheter comprising:

a first elongate tubular body having a proximal portion, a distal portion, a proximal end, a distal end, and a lumen extending between the proximal end and the distal end;

a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen, and wherein no portion of the elongate member is in the lumen of the first elongate tubular body.

2. A catheter of claim 1, wherein the catheter further comprises a third elongate tubular body having a proximal portion, a distal portion, a proximal end, a distal end, and a lumen extending between the proximal end and the distal end, the third elongate tubular body being fixedly attached on the proximal portion of the elongate member, the third elongate tubular body being proximal of the second elongate tubular body.

3. A catheter of claim 2, wherein the third elongate tubular body is tandem to the second elongate tubular body.

4. A catheter of claim 2, wherein the catheter is an embolic protection device delivery and recovery catheter.

5. A catheter of claim 2, wherein the third elongate tubular body has a longitudinal length of 5 to 30 cm.

6. A catheter of claim 2, wherein the third elongate tubular body has an outer diameter of 0.7 to 2 mm.

7. A catheter of claim 2, wherein the third elongate tubular body has a soft tip at the proximal end and the diameter of the lumen of the third elongate tubular body is reduced in the soft tip.

8. A catheter of claim 1, wherein the lumen of the first elongate tubular body has a constant diameter.

9. A catheter of claim 1, wherein the lumen of the second elongate tubular body has a constant diameter.

10. A catheter of claim 1, wherein the lumens of the first and second elongate tubular bodies have the same constant diameter.

11. A catheter of claim 1, wherein the catheter is an embolic protection device delivery catheter.

12. A catheter of claim 1, wherein the first and second elongate tubular bodies are formed of one or more polymers.

13. A catheter of claim 1, wherein the first and second elongate tubular bodies are maintained in rotational alignment with each other by cooperating structures on the elongate member and on the second elongate tubular body.

14. A catheter of claim 13, wherein the cooperating structures are a portion of the elongate member having a partial circular cross-section and a second lumen in the second elongate tubular body, the second lumen having a partial circular cross-section.

15. A catheter of claim 14, wherein the portion of the elongate member having a partial circular cross-section extends over 20 to 180 degrees of arc.

16. A catheter of claim 1, wherein the catheter has a longitudinal length of 100 to 240 cm.

17. A catheter of claim 1, wherein the catheter has a longitudinal length of 175 to 200 cm.

18. A catheter of claim 1, wherein the first elongate tubular body has a longitudinal length of 5 to 30 cm.

19. A catheter of claim 1, wherein the second elongate tubular body has a longitudinal length of 5 to 20 cm.

20. A catheter of claim 1, wherein the first elongate tubular body has an outer diameter of 0.7 to 2 mm.

21. A catheter of claim 1, wherein the second elongate tubular body has an outer diameter of 0.7 to 2 mm.

22. A catheter of claim 1, wherein the first elongate tubular body has a soft tip at the distal end.

23. A catheter of claim 1, wherein the locking mechanism comprises a finger that passes into a window on the elongate member when the second elongate tubular body and the first elongate tubular body are adjacent to each other.

24. A catheter of claim 23, wherein the second elongate tubular body comprises a window that is centered over the window of the elongate member when the second elongate tubular body and the first elongate tubular body are adjacent to each other.

25. A catheter of claim 23, wherein the finger is connected to a spring that blocks a portion of the lumen of the second elongate tubular body when the finger does not pass into the window on the elongate member.

26. A catheter of claim 25, wherein the spring does not block a portion of the lumen of the second elongate tubular body when the finger passes into the window on the elongate member.

27. A catheter of claim 25, wherein the second elongate tubular body comprises a window that is centered over the window of the elongate member when the second elongate tubular body and the first elongate tubular body are adjacent to each other, and wherein the spring does not block a portion of the lumen of the second elongate tubular body when the finger passes through the window on the elongate member and into the window of the second elongate tubular body.

28. A catheter of claim 1, wherein the elongate member is cylindrical.

29. A catheter of claim 1, wherein an outer diameter of the first elongate tubular body is constant.

30. An assembly comprising an embolic protection device and a catheter, the catheter having a proximal portion and a distal portion, the catheter comprising:

a first elongate tubular body having a proximal portion, a distal portion, a proximal end, a distal end, and a lumen extending between the proximal end and the distal end;

a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen, and wherein the embolic protection device comprises a filter.

31. An assembly of claim 30, wherein the catheter further comprises a third elongate tubular body having a proximal portion, a distal portion, a proximal end, a distal end, and a lumen extending between the proximal end and the distal end, the third elongate tubular body being fixedly attached on the proximal portion of the elongate member, the third elongate tubular body being proximal of the second elongate tubular body.

32. An assembly of claim 31, wherein the third elongate tubular body is tandem to the second elongate tubular body.

33. An assembly of claim 31, wherein the third elongate tubular body has a longitudinal length of 5 to 30 cm.

34. An assembly of claim 31, wherein the third elongate tubular body has an outer diameter of 0.7 to 2 mm.

35. An assembly of claim 31, wherein the third elongate tubular body has a soft tip at the proximal end and the diameter of the lumen of the third elongate tubular body is reduced in the soft tip.

36. An assembly of claim 30, wherein the lumen of the first elongate tubular body has a constant diameter.

37. An assembly of claim 30, wherein the lumen of the second elongate tubular body has a constant diameter.

38. An assembly of claim 30, wherein the lumens of the first and second elongate tubular bodies have the same constant diameter.

39. An assembly of claim 30, wherein the first and second elongate tubular bodies are formed of one or more polymers.

40. An assembly of claim 30, wherein the first and second elongate tubular bodies are maintained in rotational alignment with each other by cooperating structures on the elongate member and on the second elongate tubular body.

41. An assembly of claim 40, wherein the cooperating structures are a portion of the elongate member having a partial circular cross-section and a second lumen in the second elongate tubular body, the second lumen having a partial circular cross-section.

42. An assembly of claim 41, wherein the portion of the elongate member having a partial circular cross-section extends over 20 to 180 degrees of arc.

43. An assembly of claim 30, wherein the catheter has a longitudinal length of 100 to 240 cm.

44. An assembly of claim 30, wherein the catheter has a longitudinal length of 175 to 200 cm.

45. An assembly of claim 30, wherein the first elongate tubular body has a longitudinal length of 5 to 30 cm.

46. An assembly of claim 30, wherein the second elongate tubular body has a longitudinal length of 5 to 20 cm.

47. An assembly of claim 30, wherein the first elongate tubular body has an outer diameter of 0.7 to 2 mm.

48. An assembly of claim 30, wherein the second elongate tubular body has an outer diameter of 0.7 to 2 mm.

49. An assembly of claim 30, wherein the first elongate tubular body has a soft tip at the distal end.

50. An assembly of claim 30, wherein the locking mechanism comprises a finger that passes into a window on the elongate member when the second elongate tubular body and the first elongate tubular body are adjacent to each other.

51. An assembly of claim 50, wherein the second elongate tubular body comprises a window that is centered over the window of the elongate member when the second elongate tubular body and the first elongate tubular body are adjacent to each other.

52. An assembly of claim 50, wherein the finger is connected to a spring that blocks a portion of the lumen of the second elongate tubular body when the finger does not pass into the window on the elongate member.

53. An assembly of claim 52, wherein the spring does not block a portion of the lumen of the second elongate tubular body when the finger passes into the window on the elongate member.

54. An assembly of claim 52, wherein the second elongate tubular body comprises a window that is centered over the window of the elongate member when the second elongate tubular body and the first elongate tubular body are adjacent to each other, and wherein the spring does not block a portion of the lumen of the second elongate tubular body when the finger passes through the window on the elongate member and into the window of the second elongate tubular body.

55. An assembly of claim 30, wherein an outer diameter of the first elongate tubular body is constant.

56. A method for positioning a catheter within a patient's blood vessel, the method comprising:
 providing a catheter, the catheter having a proximal portion and a distal portion, the catheter comprising:
 a first elongate tubular body having a proximal portion, a distal portion, a proximal end, a distal end, and a lumen extending between the proximal end and the distal end;
 a second elongate tubular body having a proximal portion, a distal portion, a proximal end, a distal end, and a lumen extending between the proximal end and the distal end; and
 an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member,
 the second elongate tubular body being disposed on the elongate member and the second elongate tubular body being slidable along a portion of the elongate member,
 wherein the second elongate tubular body is able to be disposed in a first position so that the first and second tubular bodies are not adjacent to each other and able to be disposed in a second position so that the first and second tubular bodies are adjacent to each other, and
 wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen, providing a guide wire having a proximal end and a distal end;

advancing the guide wire to a target site within the patient's blood vessel;

disposing the guide wire proximal end within the lumen of the first elongate tubular body; and advancing the catheter over the guide wire to the target site.

57. A method of claim 56, wherein the guide wire is removed from the catheter after the catheter has been advanced to the target site.

58. A method of claim 57, wherein an embolic protection device comprising a host wire is loaded into the lumen of the second elongate tubular body, the locking mechanism being in the open configuration.

59. A method of claim 58, wherein the embolic protection device is retained in the lumen of the second elongate tubular body and does not move relative to the second elongate tubular body as a distal end of the embolic protection device is advanced distally a portion of the distance to the target site by advancing the host wire distally.

60. A method of claim 59, wherein the distal end of the second elongate tubular body is advanced by advancing the host wire distally so that the distal end of the second elongate tubular body is adjacent to the proximal end of the first elongate tubular body and the first elongate tubular body and the first and second elongate tubular bodies are locked together by the locking mechanism.

61. A method of claim 60, wherein the distal end of the embolic protection device is advanced distally by advancing the host wire distally and a portion of the embolic protection device exits the distal end of the first elongate tubular body.

62. A method of claim 61, wherein the catheter is removed from the target site while the embolic protection device remains at the target site.

63. A method of claim 62, wherein a medical procedure is performed at the target site.

64. A method of claim 63, wherein the embolic protection device is retrieved by reversing the orientation of the catheter so that the proximal portion of the catheter is closer to the target site than the distal portion of the catheter, and distally advancing the third elongate tubular body over the embolic protection device, and then removing the catheter and the embolic protection device.

65. A method of claim 56, wherein an embolic protection device comprising a host wire is loaded into the lumen of the second elongate tubular body.

66. A method for positioning a catheter within a patient's blood vessel, the method comprising:

providing a catheter, the catheter having a proximal portion and a distal portion, the catheter comprising:

a first elongate tubular body having a proximal portion, a distal portion, a proximal end, a distal end, and a lumen extending between the proximal end and the distal end;

a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, and wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen, and advancing the catheter to a target site within the patient's blood vessel using a guide catheter.

67. A method of claim 66, wherein an embolic protection device comprising a host wire is loaded into the lumen of the first elongate tubular body, the locking mechanism being in the open configuration.

68. A method of claim 67, wherein the embolic protection device is retained in the lumen of the first elongate tubular body as a distal end of the embolic protection device is advanced distally to the target site.

69. A method of claim 68, wherein the distal end of the embolic protection device is advanced distally by advancing the embolic protection device and a portion of the embolic protection device exits the distal end of the first elongate tubular body.

70. A method of claim 69, wherein the catheter is removed from the target site while the embolic protection device remains at the target site.

71. A catheter having a proximal portion and a distal portion, the catheter comprising:

a first elongate tubular body having a proximal portion, a distal portion, a proximal end, a distal end, and a lumen extending between the proximal end and the distal end;

a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen, wherein the lumen of the first elongate tubular body has a constant diameter, and wherein an outer diameter of the first elongate tubular body is constant.

72. A catheter of claim 71, wherein the lumens of the first and second elongate tubular bodies have the same constant diameter.

73. A catheter having a proximal portion and a distal portion, the catheter comprising:
   a first elongate tubular body having a proximal portion, a distal portion, a proximal end, a distal end, and a lumen extending between the proximal end and the distal end;
   a second elongate tubular body having a proximal portion, a distal portion, a proximal end, a distal end, and a lumen extending between the proximal end and the distal end; and
   an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member,
   the second elongate tubular body being disposed on the elongate member and the second elongate tubular body being slidable along a portion of the elongate member,
   wherein the second elongate tubular body is able to be disposed in a first position so that the first and second tubular bodies are not adjacent to each other and able to be disposed in a second position so that the first and second tubular bodies are adjacent to each other,
   wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen,
   wherein the lumen of the second elongate tubular body has a constant diameter, and wherein an outer diameter of the first elongate tubular body is constant.

74. A catheter having a proximal portion and a distal portion, the catheter comprising:
   a first elongate tubular body having a proximal portion, a distal portion, a proximal end, a distal end, and a lumen extending between the proximal end and the distal end;
   a second elongate tubular body having a proximal portion, a distal portion, a proximal end, a distal end, and a lumen extending between the proximal end and the distal end; and
   an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member,
   the second elongate tubular body being disposed on the elongate member and the second elongate tubular body being slidable along a portion of the elongate member,
   wherein the second elongate tubular body is able to be disposed in a first position so that the first and second tubular bodies are not adjacent to each other and able to be disposed in a second position so that the first and second tubular bodies are adjacent to each other,
   wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen, and
   wherein the first and second elongate tubular bodies are maintained in rotational alignment with each other by cooperating structures on the elongate member and on the second elongate tubular body.

75. A catheter of claim 74, wherein the cooperating structures are a portion of the elongate member having a partial circular cross-section and a second lumen in the second elongate tubular body, the second lumen having a partial circular cross-section.

76. A catheter of claim 75, wherein the portion of the elongate member having a partial circular cross-section extends over 20 to 180 degrees of arc.

77. A catheter having a proximal portion and a distal portion, the catheter comprising:
   a first elongate tubular body having a proximal portion, a distal portion, a proximal end, a distal end, and a lumen extending between the proximal end and the distal end;
   a second elongate tubular body having a proximal portion, a distal portion, a proximal end, a distal end, and a lumen extending between the proximal end and the distal end; and
   an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member,
   the second elongate tubular body being disposed on the elongate member and the second elongate tubular body being slidable along a portion of the elongate member,
   wherein the second elongate tubular body is able to be disposed in a first position so that the first and second tubular bodies are not adjacent to each other and able to be disposed in a second position so that the first and second tubular bodies are adjacent to each other,
   wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen,
   wherein the catheter further comprises a third elongate tubular body having a proximal portion, a distal portion, a proximal end, a distal end, and a lumen extending between the proximal end and the distal end, the third elongate tubular body being fixedly attached on the proximal portion of the elongate member, the third elongate tubular body being proximal of the second elongate tubular body, and wherein the third elongate tubular body has a soft tip at the proximal end and the diameter of the lumen of the third elongate tubular body is reduced in the soft tip.

78. A catheter having a proximal portion and a distal portion, the catheter comprising:

a first elongate tubular body having a proximal portion, a distal portion, a proximal end, a distal end, and a lumen extending between the proximal end and the distal end;

a second elongate tubular body having a proximal portion, a distal portion, a proximal end, a distal end, and a lumen extending between the proximal end and the distal end; and an elongate member having a proximal portion, a distal portion, a proximal end, and a distal end, the elongate member joining the first and second elongate tubular bodies, the first elongate tubular body being disposed distal and tandem to the second elongate tubular body, and the first tubular body being fixedly attached on the distal portion of the elongate member, the second elongate tubular body being disposed on the elongate member and the second elongate tubular body being slidable along a portion of the elongate member, wherein the second elongate tubular body is able to be disposed in a first position so that the first and second tubular bodies are not adjacent to each other and able to be disposed in a second position so that the first and second tubular bodies are adjacent to each other, wherein the catheter comprises a locking mechanism that is adjustable between an open configuration and a locked configuration, and when the locking mechanism is in an open configuration the first and second elongate tubular bodies are not locked together and when the locking mechanism is in a locked configuration the first and second elongate tubular bodies are adjacent to each other and locked together and the lumens of the first and second elongate tubular bodies form one continuous lumen, and wherein the locking mechanism comprises a finger that passes into a window on the elongate member when the second elongate tubular body and the first elongate tubular body are adjacent to each other.

79. A catheter of claim 78, wherein the second elongate tubular body comprises a window that is centered over the window of the elongate member when the second elongate tubular body and the first elongate tubular body are adjacent to each other.

80. A catheter of claim 78, wherein the finger is connected to a spring that blocks a portion of the lumen of the second elongate tubular body when the finger does not pass into the window on the elongate member.

81. A catheter of claim 80, wherein the spring does not block a portion of the lumen of the second elongate tubular body when the finger passes into the window on the elongate member.

82. A catheter of claim 80, wherein the second elongate tubular body comprises a window that is centered over the window of the elongate member when the second elongate tubular body and the first elongate tubular body are adjacent to each other, and wherein the spring does not block a portion of the lumen of the second elongate tubular body when the finger passes through the window on the elongate member and into the window of the second elongate tubular body.

* * * * *